(12) United States Patent
Chebator et al.

(10) Patent No.: US 8,430,843 B2
(45) Date of Patent: Apr. 30, 2013

(54) DILUENT/MEDICATION MIXING SYRINGE ASSEMBLY

(75) Inventors: Casey Chebator, Weymouth, MA (US); Richard M. Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/426,882

(22) Filed: Mar. 22, 2012

(65) Prior Publication Data

US 2012/0179095 A1    Jul. 12, 2012

Related U.S. Application Data

(63) Continuation of application No. 12/565,016, filed on Sep. 23, 2009, now Pat. No. 8,162, 875.

(60) Provisional application No. 61/101,410, filed on Sep. 30, 2008.

(51) Int. Cl.
*A61M 37/00*    (2006.01)

(52) U.S. Cl.
USPC ............................... 604/85; 604/82; 604/518

(58) Field of Classification Search .................. 604/518, 604/132, 92, 82, 85
See application file for complete search history.

(56) References Cited

U.S. PATENT DOCUMENTS

| | | | |
|---|---|---|---|
| 3,164,303 A | 1/1965 | Trautmann | |
| 5,569,193 A | 10/1996 | Hofstetter et al. | |
| 5,599,312 A | 2/1997 | Higashikawa | |
| 5,637,087 A | 6/1997 | O'Neil et al. | |
| 5,785,682 A | 7/1998 | Grabenkort | |
| 6,997,910 B2 | 2/2006 | Howlett et al. | |
| 2005/0105384 A1 | 5/2005 | Eder et al. | |
| 2005/0105385 A1 | 5/2005 | McGill et al. | |
| 2006/0079834 A1 | 4/2006 | Tennican et al. | |
| 2007/0217282 A1* | 9/2007 | Lidgren et al. | ................ 366/108 |
| 2008/0171971 A1 | 7/2008 | DiPerna et al. | |

FOREIGN PATENT DOCUMENTS

WO    99/17820    4/1999

OTHER PUBLICATIONS

Extended European Search Report dated Feb. 23, 2010 regarding European Application No. 09171803.1, 7 pages.
Office Action dated Apr. 4, 2011 regarding U.S. Appl. No. 12/565,016, 8 pages.
Amendment filed Jun. 30, 2011 regarding U.S. Appl. No. 12/565,016, 6 pages.
Final Office Action dated Sep. 28, 2011 regarding U.S. Appl. No. 12/565,016, 6 pages.

* cited by examiner

*Primary Examiner* — Kevin C Sirmons
*Assistant Examiner* — Brandy S Lee
(74) *Attorney, Agent, or Firm* — Lisa E. Winsor, Esq.

(57) ABSTRACT

A diluent/medication mixing syringe assembly is described which includes a cannula which extends through a syringe plunger assembly into a reservoir of the syringe assembly. The cannula facilitates injection of a diluent, medication or other fluid into the fluid reservoir of the syringe assembly immediately prior to use for mixing with a medication in the reservoir. In one embodiment, a mixing element is secured to a distal end of the cannula within the reservoir to improve mixing efficiency.

18 Claims, 5 Drawing Sheets

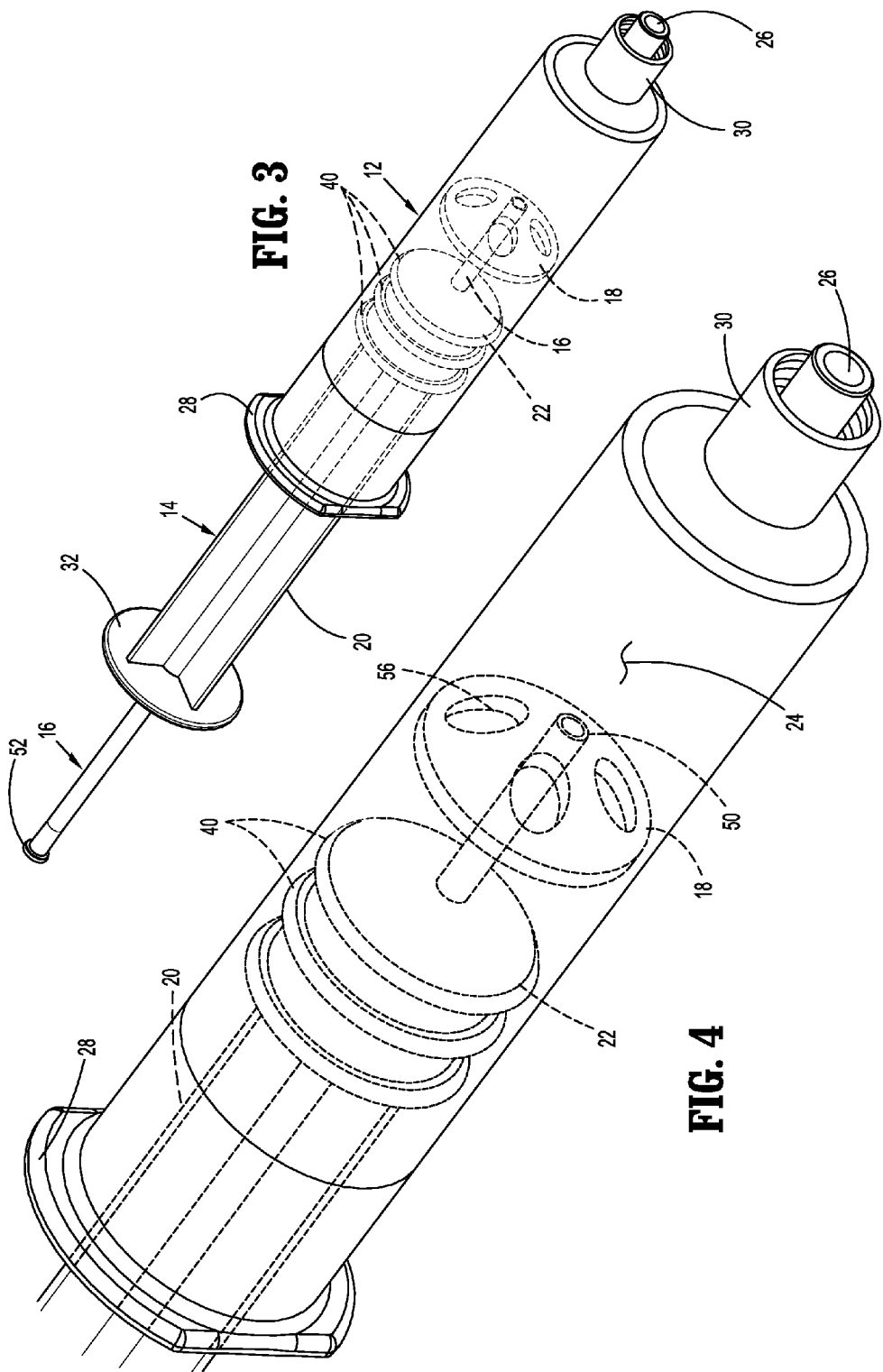

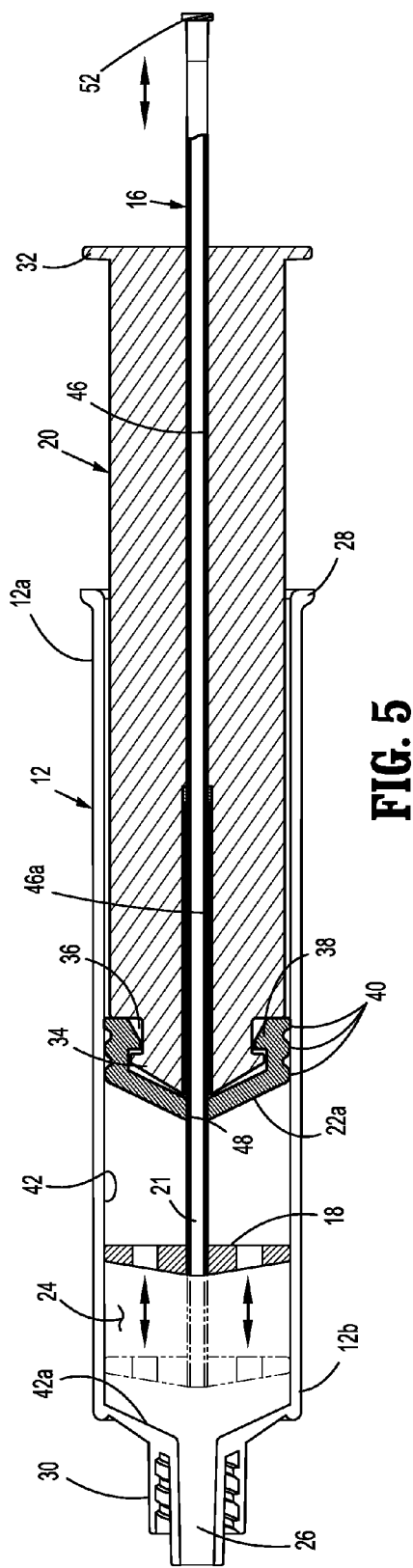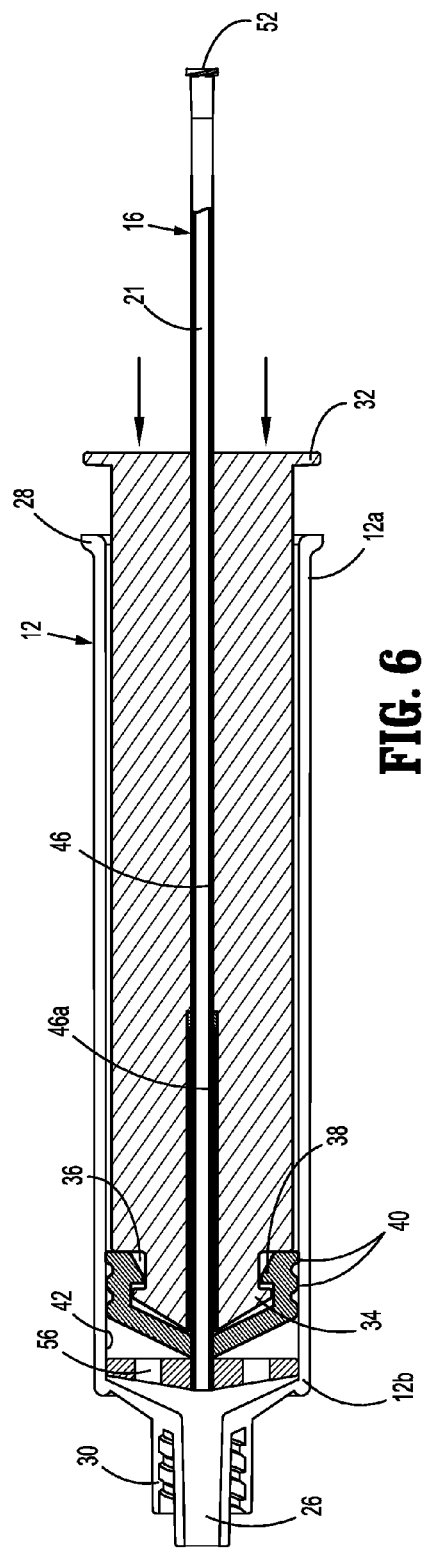

DILUENT/MEDICATION MIXING SYRINGE ASSEMBLY

CROSS-REFERENCE TO RELATED APPLICATIONS

This application is a continuation application of and claims priority under 35 U.S.C. §120 to co-pending U.S. application Ser. No. 12/565,016 filed Sep. 23, 2009, entitled DILLUENT/MEDICATION MIXING SYRINGE ASSEMBLY, which claims priority under U.S.C. 120 to U.S. application Ser. No. 61/101,410 which was filed on Sep. 30, 2008, entitled DILLUENT/MEDICATION MIXING SYRINGE ASSEMBLY, the entire contents of each of which are incorporated herein in their entireties by reference for all purposes.

BACKGROUND

1. Technical Field

The present disclosure relates generally to syringes and, more particularly, to a syringe including a cannula for delivering a diluent or additional medication into the syringe.

2. Background of Related Art

Syringe assemblies which include two chambers for separately storing a diluent and a medication are well known in the art. Typically, multi-chamber syringes which separately store a diluent and a medication are required with medications which are poorly soluble or insoluble in an aqueous solution, medications which lack sufficient physical or chemical stability when stored for a prolonged period of time, or medications which include active ingredients which undergo degradation due to interaction with a suspension medium. Such medications are typically stored in a syringe assembly in a dry, lyophilized state separate from a diluent.

Although multi-chamber syringes have proven effective for mixing medications in powder form with a diluent immediately prior to injection into a venous catheter or related device, such syringes typically are complex and, thus, are expensive to manufacture.

Accordingly, a continuing need exists in the medical arts for a syringe assembly which has the capability of mixing a diluent with a medication immediately prior to injection, which is less complex and provides improved mixing capabilities.

SUMMARY

A diluent/medication mixing syringe assembly is disclosed which includes a syringe body having an open proximal end and a fluid outlet on a distal end and a plunger assembly including a plunger body and a plunger head supported on a distal end of the plunger body. The plunger head is slidably and sealingly engaged with an inner wall of the syringe body to define a reservoir in the distal end of the syringe body. A cannula is supported on and extends through the plunger assembly. The cannula defines a longitudinal channel which extends through the plunger assembly into the reservoir. In one embodiment, the plunger rod and the plunger head define a longitudinal bore which is dimensioned to receive the cannula. The cannula can be slidably positioned within the longitudinal bore such that the distal end of the cannula is movable axially within the reservoir. The cannula can also be rotatably positioned within the longitudinal bore.

In one embodiment, a mixing element is supported on the distal end of the cannula within the reservoir. The mixing element can include at least one orifice which extends through the mixing element and is configured to cause turbulence within the reservoir when the cannula is moved axially and/or rotated. The at least one orifice can include a plurality of orifices.

In one embodiment, the proximal end of the cannula includes an adaptor which is configured to releasably engage a supply of fluid. The adaptor can be a female luer type connector.

The syringe assembly can include a sealing member positioned within the longitudinal bore of the plunger rod about the cannula. In one embodiment, the cannula is separable from the syringe assembly and the seal member is configured to seal the longitudinal bore of the plunger assembly when the cannula is separated.

In one embodiment, a male luer connector is positioned on the distal end of the syringe body about the fluid outlet.

A method of mixing a diluent (or additional medication) with a medication in a syringe assembly is also disclosed. The method includes the steps of i) providing a syringe assembly including a syringe body and a plunger assembly wherein the syringe body has an open proximal end and a fluid outlet disposed in the distal end, the plunger assembly includes a plunger body and a plunger head supported on a distal end of the plunger body, the plunger head being slidably and sealingly engaged with an inner wall of the syringe body and defining a reservoir with the syringe body in a distal end of the syringe body, and a cannula extending through the plunger assembly, the cannula defining a longitudinal channel disposed within the reservoir; ii) providing a medication within the reservoir; and iii) introducing a diluent or additional medication into the reservoir via the cannula. In one embodiment, the step of providing a syringe assembly includes providing a mixing element on the distal end of the cannula, wherein the method further includes the step of moving the mixing element within the reservoir to mix the diluent (or additional medication) and the medication. In one embodiment, the medication is in powder form. In one embodiment, the method includes the step of disconnecting the cannula from the syringe assembly after the step of moving the mixing element.

BRIEF DESCRIPTION OF THE DRAWINGS

Various embodiments of the presently disclosed diluent/medication mixing syringe assembly are disclosed herein with reference to the drawings, wherein:

FIG. 3 is a side perspective view from the distal end of the diluent/medication mixing syringe assembly shown in FIG. 1 illustrating the distal end of the plunger assembly and mixing disc in phantom;

FIG. 4 is an enlarged perspective view of the distal end of the diluent/medication mixing syringe assembly shown in FIG. 3 illustrating the distal end of the plunger assembly and mixing disc in phantom;

FIG. 5 is a side cross-sectional view of the syringe assembly shown in FIG. 1 during movement of the mixing disc within the reservoir with the plunger assembly in a retracted position;

FIG. 6 is a side cross-sectional view of the syringe assembly shown in FIG. 1 with the plunger assembly in an advanced position.

DETAILED DESCRIPTION OF EMBODIMENTS

Figure 1:
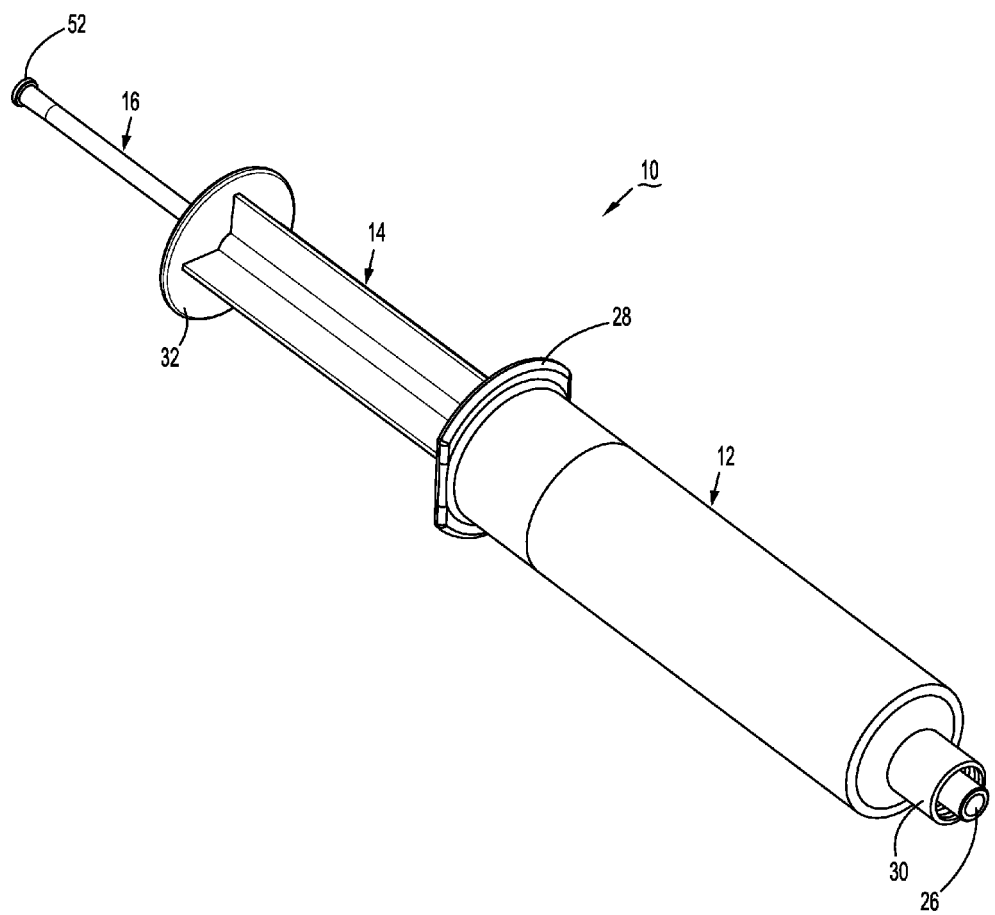
FIG. 1 is a side perspective view from the distal end of one embodiment of the presently disclosed diluent/medication mixing syringe assembly.

Embodiments of the presently disclosed diluent/medication mixing syringe assembly and its method of use will now be described in detail with reference to the drawings wherein like reference numerals designate identical or corresponding elements in each of the several views. In this description, the term proximal is generally used to indicate the relative nearness of a referenced item to a user of the device and the term distal is used to indicate the relative remoteness of a referenced item to a user of the device.

Figure 2:
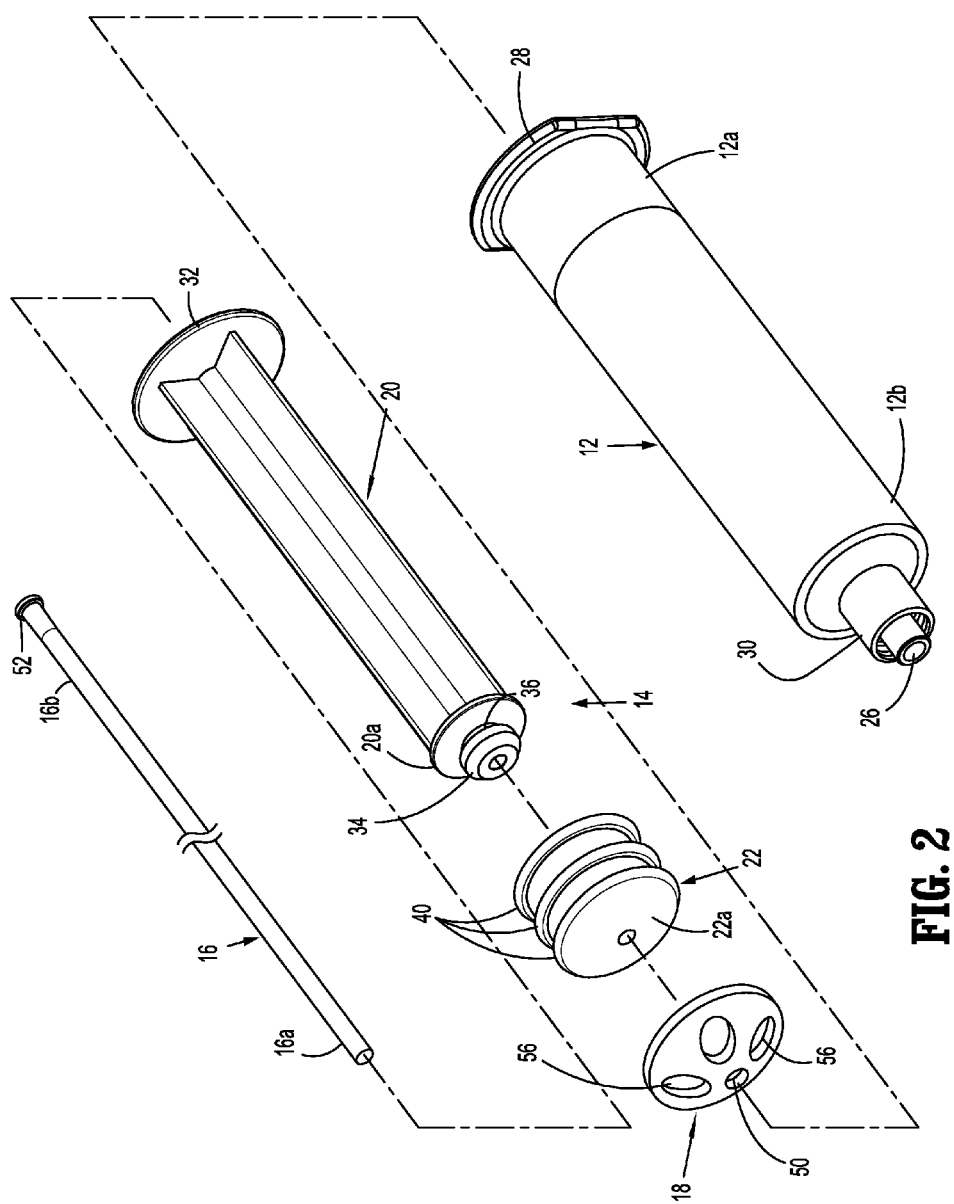
FIG. 2 is a side perspective exploded view from the distal end of the diluent/medication mixing syringe assembly shown in FIG. 1.

FIGS. 1-7 illustrate one embodiment of the presently disclosed diluent/medication mixing syringe assembly shown generally as 10. Briefly, referring to FIGS. 1 and 2, syringe assembly 10 includes a syringe body 12, a plunger assembly 14, a cannula 16 and a mixing element 18 (FIG. 2). Plunger assembly 14 includes a plunger body 20 and a plunger head 22 which is secured to a distal end 20a of plunger body 20. Plunger head 22 is slidably positioned within syringe body 12 to define a reservoir 24 (FIG. 5) within the distal end of syringe body 12 as will be discussed in further detail below.

Syringe body 12 has an open proximal end 12a dimensioned to slidably receive plunger body 20 and a distal end 12b defining a fluid outlet 26. A gripping flange 28 is positioned about proximal end 12a of syringe body 12. A male luer connector 30 or related structure is formed about fluid outlet 26 on distal end 12b of syringe body 12. A cap (not shown) is provided to seal fluid outlet 26 prior to use of syringe assembly 10.

Referring also to FIGS. 2-5, plunger body 20 has a proximal end which includes a finger engagement member 32 and a distal end adapted to receive plunger head 22. In one embodiment, the distal end of plunger body 20 includes a stepped portion 34 defining an annular recess 36 dimensioned to receive a proximal annular rib 38 (FIG. 5) formed on plunger head 22. Plunger head 22 is formed of a resilient material, e.g., rubber, which is stretched over stepped portion 34 such that annular rib 38 is received within annular recess 36 to secure plunger head 22 onto the distal end of plunger body 20. Alternatively, plunger head 22 and plunger body 20 may have a variety of different configurations for securing plunger head 22 to plunger body 20. The external surface of plunger head 22 includes one or more ribs 40, e.g., three. Ribs 40 are dimensioned to slidably and sealingly engage an inner wall 42 (FIG. 5) of syringe body 12. Reservoir 24 is defined between a distal face 22a of plunger head 22 and a distal end 42a (FIG. 5) of inner wall 42 of syringe body 12.

Referring to FIG. 5, plunger body 20 defines a longitudinal bore 46 which extends the entire length of body 20. Plunger head 22 also defines a bore 48 which is axially aligned with bore 46. Bores 46 and 48 are dimensioned to slidably receive cannula 16 as will be discussed in further detail below.

Cannula 16 is substantially rigid and defines a longitudinal channel 21. Cannula 16 is slidably positioned through bores 46 and 48 of plunger body 20 and plunger head 22, respectively. A distal end 16a of cannula 16 is movably positioned within reservoir 24 at a position distally of plunger head 22. Mixing element 18 includes a central bore 50 (FIG. 2). Distal end 16a of cannula 16 is received and secured within central bore 50 of mixing element 18 using any known fastening technique, e.g., adhesives, crimping, welding, etc., such that axial and/or rotational movement of cannula 16 effects corresponding axial and/or rotational movement of mixing element 18. A proximal end 16b of cannula 16 includes an adaptor 52 which is configured to releasably engage a supply of diluent. Adaptor 52 may include a female luer type connector or like structure. Although not shown, the adaptor 52 may releasably receive a cap (not shown) for sealing proximal end 16b of cannula 16.

As discussed above, mixing element 18 is secured to the distal end of cannula 16. In one embodiment, mixing element 18 is disc-shaped and includes one or more orifices 56 which extend through mixing element 18. When cannula 16 is moved axially to move mixing element 18 axially within reservoir 24 (FIG. 5), turbulence is created within the mixture located within reservoir 24 to improve the mixing efficiency of the medication and the diluent. In one embodiment, orifices 56 define axes which are angled with respect to a longitudinal axis of cannula 16 such that axial movement of mixing element 18 causes the mixture within reservoir 24 to swirl.

Figure 7:
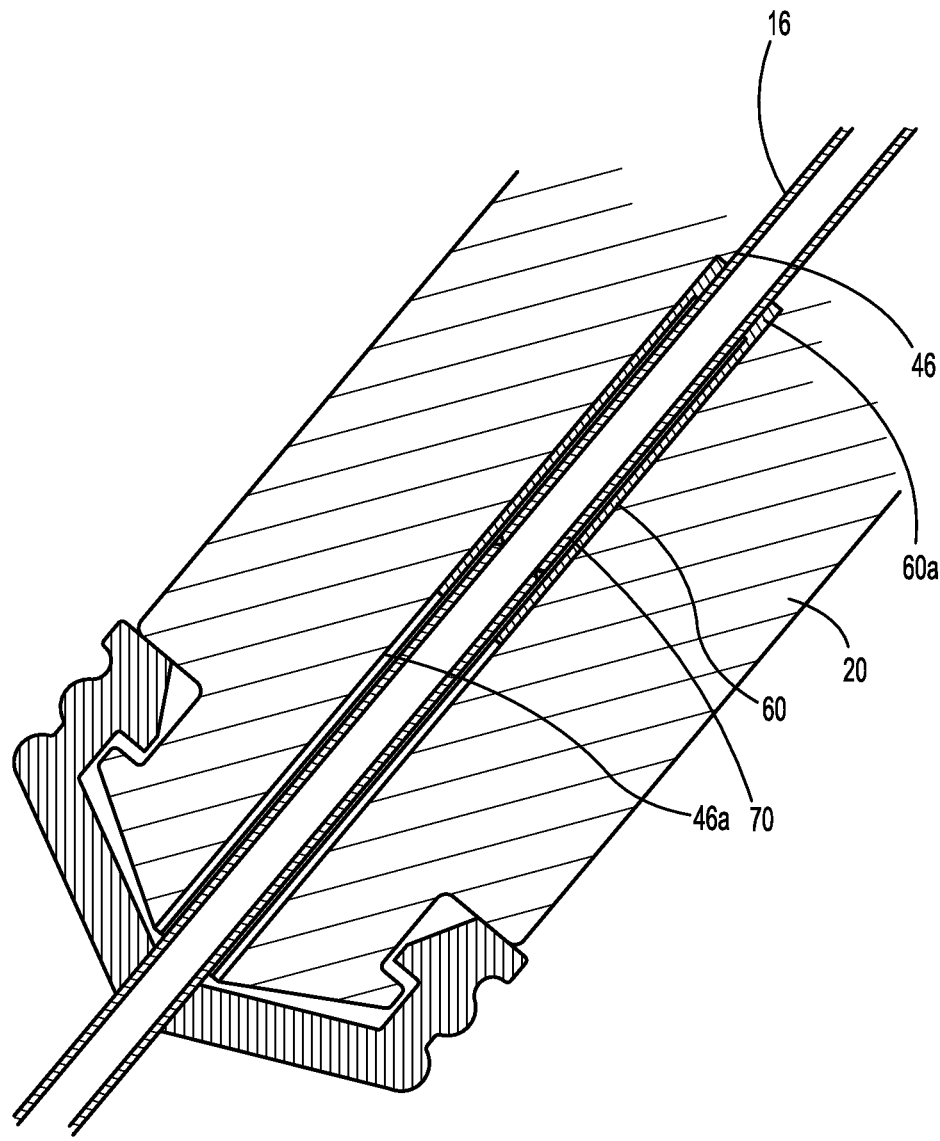
FIG. 7 is an enlarged cross-sectional view of the distal end of the plunger assembly.

Referring to FIG. 7, a sealing member 60 is supported within longitudinal bore 46 of plunger body 20. As illustrated, bore 46 may include a stepped portion 46a which receives sealing member 60. In one embodiment, sealing member 60 has a proximal end 60a which includes an inwardly extending annular rib which slidably and sealingly engages an outer surface of cannula 16. Sealing member 60 can be formed of a resilient material which closes or seals bore 46 of plunger body 20 in the event cannula 16, or a proximal portion thereof, is separated from syringe assembly 10. In that respect, cannula 16 may include a frangible or weakened portion 70 which allows separation of the proximal portion of cannula 16 from the distal portion of cannula 16 upon application of a predetermined axial or torsional force on the proximal end of cannula 16. The predetermined force should be selected to prevent inadvertent separation of the distal and proximal portions of the cannula while facilitating separation by medical personnel. Such predetermined force can be from about two to about five pounds.

Referring to FIGS. 3-6, syringe assembly 10 may be provided with a medication in reservoir 24 which may be in powder form. Alternatively, medication can be drawn into reservoir 24 using known techniques. Prior to use, a cap is provided over fluid outlet 26 and over proximal end 16b of cannula 16. In use, with a medication positioned within reservoir 24, and a cap (pot shown) secured to male luer adaptor 30 over fluid outlet 26, the cap (not shown) over proximal end of cannula 16 is removed. Next, a diluent (or additional medication) is introduced through cannula 16 into reservoir 24. Then, adaptor 30 is resealed and cannula 16 is moved axially and/or rotated to move mixing element 18 within reservoir 24 to effectuate mixing of the medication and the diluent (or additional medication). In one embodiment, as discussed above, the proximal portion of the cannula 16 can be separated from the distal portion of the cannula when adequate mixing has been affected. Thereafter, as shown in FIG. 6, the cap (not shown) over fluid outlet 26 can be removed and plunger assembly 14 can be actuated to dispense the mixture within reservoir 24 through outlet 26.

It will be understood that various modifications may be made to the embodiments disclosed herein. For example, a variety of different seal configurations can be used to seal about the cannula. Therefore, the above description should not be construed as limiting, but merely as exemplifications of preferred embodiments. Those skilled in the art will envision other modifications within the scope and spirit of the claims appended hereto.

What is claimed is:

1. A diluent/medication mixing syringe assembly comprising:
- a syringe body having an inner wall, an open proximal end, and a distal end opposite the proximal end having a fluid outlet;
- a plunger assembly including a plunger body and a plunger head extending from a distal end of the plunger body, the plunger head slidably and sealingly engaging the inner wall of the syringe body, the plunger head, the distal end of the syringe body and the inner wall between the plunger head and distal end defining a reservoir within the syringe body, the plunger head and the plunger body having a longitudinal bore extending therethrough;
- a cannula extending through the bore extending through the plunger head and the plunger body, the cannula having a longitudinal channel extending through the plunger assembly and into the reservoir;
- a mixing element secured to a distal end of the cannula and positioned in the reservoir; and
- a sealing member positioned in the longitudinal bore of the plunger body around the cannula, the sealing member being formed of a resilient material and configured to seal the longitudinal bore when a proximal portion of the cannula is removed from the longitudinal bore.

2. The syringe assembly according to claim 1, wherein the cannula is slidably received in the longitudinal bore such that the distal end of the cannula is axially movable within the reservoir.

3. The syringe assembly according to claim 2, wherein the cannula is rotatably received in the longitudinal bore such that the distal end of the cannula is rotatable within the reservoir.

4. The syringe assembly according to claim 3, wherein the mixing element includes an orifice configured to cause turbulence in the reservoir when the cannula is rotated or moved axially within the reservoir.

5. The syringe assembly according to claim 4, wherein the orifice includes a plurality of orifices.

6. The syringe assembly according to claim 5, wherein each of the plurality of orifices has an axis that is angled with respect to a longitudinal axis of the cannula.

7. The syringe assembly according to claim 1, wherein a proximal end of the cannula includes an adaptor configured to releasably engage a supply of fluid.

8. The syringe assembly according to claim 7, wherein the adaptor is a female luer connector.

9. The syringe assembly according to claim 1, wherein the cannula includes a weakened portion adapted to facilitate separation of the proximal portion of the cannula from a distal portion of the cannula upon application of a predetermined force on the cannula.

10. The syringe assembly according to claim 9, wherein the predetermined force is in a range between about two pounds and about five pounds.

11. The syringe assembly according to claim 10, further comprising a male luer connector positioned on the distal end of the syringe body about the fluid outlet.

12. The syringe assembly according to claim 1, wherein the cannula is movable in the reservoir independent of the plunger assembly.

13. The syringe assembly according to claim 1, wherein the cannula extends from its distal end in the reservoir to a proximal end located proximal to the plunger body.

14. A diluent/medication mixing syringe assembly comprising:
- a syringe body having an open proximal end and a distal end including a fluid outlet;
- a plunger assembly including a plunger body and a plunger head supported on a distal end of the plunger body, the plunger assembly defining a longitudinal bore extending along an entire length of the plunger body and an entire length of the plunger head, the plunger head being adapted to slidably and sealingly engage an inner wall of the syringe body, the plunger head and the syringe body defining a reservoir at the distal end of the syringe body, the reservoir being adapted to retain a medication;
- a cannula slidably and rotatably positioned in the longitudinal bore of the plunger assembly, the cannula extending from a distal end located in the reservoir through the plunger assembly to a proximal end located proximal to the plunger assembly, the cannula being movable axially and rotatable within the plunger assembly independent of movement of the plunger assembly, the cannula defining a longitudinal channel extending through the plunger assembly into the reservoir, the proximal end of the cannula being adapted to releasably engage a supply of fluid for mixing with the medication in the reservoir; and
- a mixing element positioned in the reservoir and secured to the distal end of the cannula, the mixing element being movable with the cannula independent of the plunger assembly, the mixing element being configured to mix the medication in the reservoir with fluid introduced into the reservoir through the cannula from the supply of fluid.

15. The syringe assembly according to claim 14, further comprising a sealing member positioned within the longitudinal bore of the plunger assembly about the cannula.

16. The syringe assembly according to claim 15, wherein the sealing member is formed of a resilient material and is configured to seal the longitudinal bore upon removal of at least a proximal portion of the cannula from the longitudinal bore.

17. The syringe assembly according to claim 16, wherein the cannula includes a weakened portion adapted to facilitate separation of the proximal portion of the cannula from a distal portion of the cannula upon application of a predetermined force on the cannula.

18. A diluent/medication mixing syringe assembly comprising:
- a syringe body having an inner wall, an open proximal end, and a distal end opposite the proximal end having a fluid outlet;
- a plunger assembly including a plunger body and a plunger head extending from a distal end of the plunger body, the plunger head slidably and sealingly engaging the inner wall of the syringe body, the plunger head, the distal end of the syringe body, and the inner wall between the plunger head and distal end defining a reservoir within the syringe body;
- a cannula extending through the plunger assembly having a longitudinal channel extending through the plunger assembly and into the reservoir, the cannula including a weakened portion adapted to facilitate separation of the proximal portion of the cannula from a distal portion of the cannula upon application of a predetermined force on the cannula; and
- a mixing element secured to a distal end of the cannula and positioned in the reservoir.

* * * * *